US006183701B1

(12) United States Patent
Sherman (10) Patent No.: US 6,183,701 B1
(45) Date of Patent: *Feb. 6, 2001

(54) METHOD OF AND APPARATUS FOR MANUFACTURING METHANOL

(75) Inventor: Jeffrey H. Sherman, Dallas, TX (US)

(73) Assignee: GRT, Inc., The Woodlands, TX (US)

( * ) Notice: Under 35 U.S.C. 154(b), the term of this patent shall be extended for 0 days.

This patent is subject to a terminal disclaimer.

(21) Appl. No.: 09/368,404

(22) Filed: Aug. 4, 1999

Related U.S. Application Data

(63) Continuation-in-part of application No. 09/224,394, filed on Dec. 31, 1998, which is a continuation-in-part of application No. 09/058,494, filed on Apr. 10, 1998.

(51) Int. Cl.$^7$ ........................................... B01J 19/08
(52) U.S. Cl. .................. 422/186.3; 422/186; 210/788
(58) Field of Search ........................ 422/186, 186.3; 210/788

(56) References Cited

U.S. PATENT DOCUMENTS

| | | | |
|---|---|---|---|
| 3,773,659 | 11/1973 | Carlson et al. | 210/7 |
| 4,069,147 | 1/1978 | Abrams et al. | 210/6 |
| 4,132,637 | 1/1979 | Key et al. | 210/7 |
| 4,287,070 | 9/1981 | Pollock | 210/626 |
| 4,399,027 | * 8/1983 | Miller | 210/788 |
| 4,624,791 | 11/1986 | Ferriss | 210/704 |
| 4,744,890 | * 5/1988 | Miller et al. | 210/788 |
| 4,861,471 | 8/1989 | Nakao et al. | 210/182 |
| 4,888,101 | 12/1989 | Cooper | 204/157.15 |
| 4,966,759 | 10/1990 | Robertson et al. | 422/186 |
| 4,968,429 | 11/1990 | Yen | 210/637 |
| 5,137,607 | * 8/1992 | Anderson et al. | 422/186 |
| 5,156,173 | 10/1992 | Keyser et al. | 134/61 |
| 5,254,253 | 10/1993 | Behmann | 210/607 |
| 5,271,810 | 12/1993 | Keyser et al. | 202/185 |
| 5,316,682 | 5/1994 | Keyser et al. | 210/649 |
| 5,510,544 | 4/1996 | Keyser | 570/125 |
| 5,529,701 | 6/1996 | Grisham et al. | 210/787 |
| 5,531,904 | 7/1996 | Grisham et al. | 210/703 |
| 5,658,458 | 8/1997 | Keyser et al. | 210/195 |
| 5,662,811 | 9/1997 | Grisham et al. | 210/788 |
| 5,689,798 | * 11/1997 | Oeste | 422/186.3 |
| 5,720,858 | 2/1998 | Noceti et al. | 204/157.6 |
| 6,047,543 | * 4/2000 | Caren et al. | 422/186.04 |

OTHER PUBLICATIONS

Article titled "Pplatinum Catalysts for the High–Yield Oxidation od Methane to a Methanol Derivative" by Roy A. Periana dated May 24, 1998 published in Science vol. 280.

Article titled Progress Report: Investigation of the Partial Oxidation of Methane to Methanol in a Simulated Countercurrent Moving Bed Reactor bythe National Center For Environmental Research And Quality Assurance.

Article titled "Photocatalytic Degradation of 2–Chlorophenol in TiO2 Aqueous Suspension: Modeling of Reaction Rate" by I. Rideh published 1997 in American Chemical Society.

Article titled "Photocatalytic Degradation of Water Organic pollutants. Kinetic modeling and Energy Efficiency" by B. Serrano published 1997 in American Chemical Society.

(List continued on next page.)

Primary Examiner—Kathryn Gorgos
Assistant Examiner—Thao Tran
(74) Attorney, Agent, or Firm—Michael A. O'Neil (57) ABSTRACT

In a method of and apparatus for manufacturing methanol and higher alcohols from natural gas a catalytic area is formed on the exterior of a gas permeable partition. Natural gas is maintained on the interior of the gas permeable partition at predetermined pressure. Relative movement between the gas permeable partition and the water forms sub-micron sized bubbles of natural gas. Electromagnetic radiation is directed onto the catalytic surface to form hydroxyl radicals from the water. Methyl, ethyl, and propyl ions from the natural gas combine with the hydroxyl ions to form methanol, ethanol, and propanol.

34 Claims, 6 Drawing Sheets

OTHER PUBLICATIONS

Article titled "Simplified Modeling of Radiant Fields in Heterogeneous Photoreactors.1.Case of Zero Reflectance" by Alberto Brucato published 1997 American Chemical Society.

Article titled "Cylindrical Photocatalytic Reactors. Radiation Absorption and Scattering Effects Produced by Suspended Fine Particle in an Annular Space" by Roberto L. Romero published 1997 American Chemical Society.

Article titled "Efficient photo–assisted Fenton catalysis mediated by Fe ions on Nafion membranes active in the abatement of non–biodegradable azo–dye" by Javier Fernandez published 1998 in Chemical Commun.

Article titled "Kinetic Analysis of the Photocatalytic Degradation of Gas–Phase 2–propanol under Mass Transport–Limited Conditions with a TiO2 Film Photocatalyst" by Yoshihisa Ohko published 1998 in the J. Physi. Chem.

Article titled "Time–Dependent Behavior of Active Oxygen Species Formed on Photoirridiated TiO2 Films in Air" by Ken–ichi–Ishibashi published Mar. 19, 1998 in vol. 102, No. 12 of the Journal of Physical Chemistry B.

Article titled "Kinetics of Photocatalytic Reactions under extremely Low Intensity UV Illumination on Titanium Dioxide Thin Films" by Yoshihisa Ohko published 1997 J. Phys.Chem A.

Article titled "Preparation of a New Nanostructured TiO2 Surface Using a Two–Dimensional Array–Based Template" by Sachiko Matsushita published 1997 in The Chemical Society of Japan.

Article titled "Electronic Structure of Discrete Pseudotetrahedral Oxovanadium Centers Dispersed ina Silica Xerogel Matrix: Implications for Catalysis and Photocatalysis" by Kim Tran published 1995 in American Chemical Journal.

Article titled "Water Purification by Simiconductor Photocatalysis" by Andrew Mills published 1993 in Chemical Society Reviews.

Article titled "Low–Temperature Nonoxidative Activation of Methane over H–Galloaluminsilicate (MFI) Zeolite" by Vasant R. Choudhary published Feb. 1997 by the American Association for the Advancement of Science.

Article titled "Semiconductor Photocatalysis" by Claire Jones found on the nternet at www.warwick.ac.uk/~msrjn/fsmic.html.

Article titled "Factors Affecting Photocatalysis on Mesoporous Titanium Dioxide" by Victor Frank Stone, Jr. dated 1997 found on the internet at wwwl.che.ufl.edu/meeting/1997/annual/session/275/y/index.html.

Article titled "Solar Chemical Process Engineering" found on the internet at http://chemengineer.tqn.com/library/weekly/aa063097.htm.

Article titled "Titanium Dioxide Photocatalysis: Developing Remediation Technology for Multiple Wastes" by Tricia Drob found on the internet at http://geology.wright.edu/geology/cgwm/iris/Waterline/p.9.html.

Article titled "Photochemical Treatment of Pollutants" found on the internet at http://www.nrel.gov.research/industrial tech/pollution.html.

Article titled "Though a glass, not so darkly" found on the internet at http://ci.mond.org/9518/951811.html.

Article titled "Green Technology for the 21st Century Photocatalysts" found on the internet at http://www.entr.wisc.edu/interd/wcp/Photocatalysts.html.

Article entitled "Photochemical Conversion of Methane" from the Journal of Molecular Catalysis, pp. 371–379 by Kotaro Ogura and Makoto Kataoka no month available.

Article entitled "Conversion of Methane to Oxygen–Containing Compounds by the Photochemical Reaction" from Ind. Eng. Chem. Reg., pp. 1387–1390 by Kotaro Ogura, Catharina T. Migta and Minoru Fujita no month available.

Article entitled "Hydrogen Generation Using Cu(II)/WO3 and Oxalic Acid by Visible Light" from Hydrogen Energy, pp. 677–680 by P. Maruthamuthu and M. Ashokkumar no month available.

Article entitled "Hydrogen Production with Visible Light Using Metal Loaded–WO3 and MV2+ in Aqueous Medium" from Hydrogen Energy, pp. 275–277 by P. Maruthamuthu and M. Ashokkumar no month available.

Article entitled "Photocatalytic Hydrogen Production with Semiconductor Particulate Systems: An Effort to Enhance the Effeciency" from Int. J. Hydrogen Energy, pp. 591–595 by P. Maruthamuthu and M. Ashokkumar no month available.

Article entitled "Doping Effects of Transition Metal Ions on the Photosensitization of WO3 Particles" from Solar Energy Materials, pp. 433–438 by Pichai Maruthamuthu and Muthupandian Ashokkumar no month available.

Articled entitled "Factors Influencing the Photocatalytic Efficiency of WO3 Particles" from Journal of Photochemistry and Photobiology, A: Chemistry, pp. 249–258 by M. Ashokkumar and P. Maruthamuthu no month available.

Article entitled "Visible Light Induced Water Cleavage in Colloidal Solutions of Chromium–Doped Titanium Dioxide Particles" from J. Am. Chem. Soc., pp. 2996–3002 by Enrico Borgarello, John Kiwi, Michael Gratzel, Ezio Pelizzetti and Mario Visca no month available.

Articled entitled "Electron Transfer Reactions and Flat–Band Potentials of WO3 Colloids" from J. Phys. Chem., pp. 5827–5830 by M.T. Nenadovic, T. Rajh, O.I. Mieie, and A.J. Nozik no month available.

* cited by examiner

METHOD OF AND APPARATUS FOR MANUFACTURING METHANOL

CROSS REFERENCE TO RELATED APPLICATIONS

This application is a continuation-in-part of prior application Ser. No. 09/224,394 filed Dec. 31, 1998, currently pending which is a continuation-in-part of prior application Ser. No. 09/058,494, filed Apr. 10, 1998, currently pending.

TECHNICAL FIELD

This invention relates generally to the manufacture of methanol, and more particularly to a method of and apparatus for manufacturing methanol from methane, and to a method of and apparatus for manufacturing methanol, ethanol, and propanol from natural gas.

BACKGROUND AND SUMMARY OF THE INVENTION

Methanol, the simplest of the alcohols, is a highly desirable substance which is useful as a fuel, as a solvent, and as a feedstock in the manufacture of more complex hydrocarbons. In accordance with the method of methanol manufacture that is currently practiced in the petroleum industry, methane is first converted to synthesis gas, a mixture of carbon monoxide and hydrogen. The synthesis gas is then converted over an alumina-based catalyst to methanol. The formation of synthesis gas from methane is an expensive process.

Although often identified as methane, the feedstock for the foregoing synthesis gas process is typically natural gas. As is well known, natural gas often contains significant percentages of sulphur. Since sulphur poisons the catalyst required for its operation, the synthesis gas process for making methanol is further limited by the scarcity of low sulphur natural gas.

As will be apparent, methane and methanol are closely related chemically. Methane comprises a major component of natural gas and is therefore readily available. Despite the advantages inherent in producing methanol directly from methane, no commercially viable system for doing so has heretofore been developed.

The present invention comprises a method of and apparatus for manufacturing methanol from methane or natural gas which overcomes the foregoing and other deficiencies which have long since characterized the prior art. The method involves a gas permeable partition upon which a light-activated catalyst capable of producing hydroxyl radicals from water is deposited, it being understood that as used herein the term "light-activated catalyst" means any catalyst that is activated by electromagnetic radiation regardless of wave length.

Water is present on the catalyst side of the partition and methane or natural gas at positive pressure is present on the opposite side of the partition. The catalyst is exposed to radiation while relative movement is effected between the water and the partition. The radiation-exposed catalyst reacts with the water molecules to form hydroxyl radicals. The gas is forced through the semipermeable partition forming small bubbles in the water. The hydroxyl radicals in the water then undergo a free-radical reaction with the methane in the water to form methanol, and if natural gas is used in the process, ethanol and propanol.

In accordance with the broader aspects of the invention there is generated a stream of sub-micron sized gas bubbles. Due to their extremely small size, the gas bubbles present an extremely large surface area which increases reaction efficiency. Smaller pores in the gas permeable partition facilitate the formation of smaller bubbles. Additionally, higher relative velocity across the partition surface aids in shearing the bubbles off the surface while they are still small.

In accordance with first, second, and third embodiments of the invention, a gas permeable tube has an exterior coating comprising a titanium-based catalyst. The gas permeable tube is positioned within a glass tube and water is caused to continuously flow through the annular space between the two tubes. Methane or natural gas is directed into the interior of the gas permeable tube and is maintained at a pressure high enough to cause gas to pass into the water and prevent the flow of water into the interior of the gas permeable tube. As the water passes over the gas permeable tube, gas bubbles are continually sheared off of its surface. The gas bubbles thus generated are sub-micron in size and therefore present an extremely large surface area.

Electromagnetic radiation generated, for example, by ultraviolet lamps is directed through the glass tube and engages the titanium-based catalyst to generate hydroxyl radicals in the flowing water. The hydroxyl radicals undergo a free-radical reaction with the methane forming methanol, among other free-radical reaction products. Subsequently, the methanol and other products are separated from the reaction mixture by distillation.

In accordance with a fourth embodiment of the invention, there is provided a hollow disk which supports a gas permeable partition having an exterior coating comprising a titanium-based catalyst. The disk is positioned within a water filled container. Methane or natural gas is directed into the interior of the disk and is maintained at a pressure high enough to cause gas to pass outwardly through the partition and into the water and to prevent the flow of water into the interior of the disk.

The disk and the partition are moved at high speed relative to the water. As the gas permeable partition moves relative to the water, gas bubbles are continually sheared off of its surface. The gas bubbles thus generated are sub-micron in size and therefore present an extremely large surface area.

Electromagnetic radiation generated, for example, by ultraviolet lamps within the container engages the titanium-based catalyst to generate hydroxyl radicals in the water. The hydroxyl radicals undergo a free-radical reaction with the methane forming methanol, and, if natural gas is used in the process, ethanol and propanol. Subsequently, the methanol and other reaction products are separated from the reaction mixture by distillation.

BRIEF DESCRIPTION OF THE DRAWINGS

A more complete understanding of the invention may be had by reference to the following Detailed Description when taken in conjunction with the accompanying Drawings wherein.

DETAILED DESCRIPTION

Figure 1:
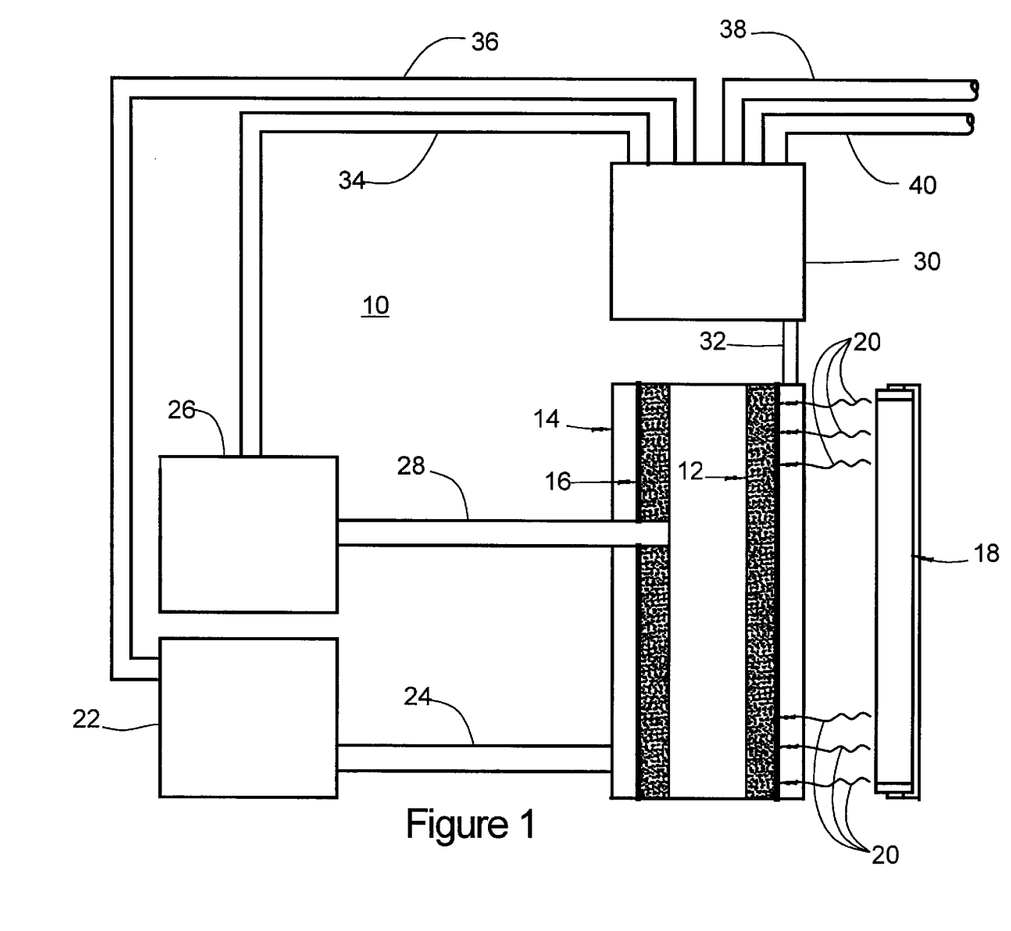
FIG. 1 is a diagrammatic illustration of a method and apparatus for manufacturing methanol comprising a first embodiment of the present invention.

Referring now to the Drawings, and particularly to FIG. 1 thereof, there is shown an apparatus for manufacturing methanol 10 comprising a first embodiment of the invention. The apparatus 10 includes a gas permeable tube 12 positioned within a glass tube 14. The tube 12 can comprise sintered stainless steel, or sintered glass, sintered ceramic materials, or a photocatalytic material. As illustrated in FIG. 1, both the gas permeable tube 12 and the glass tube 14 comprise right circular cylinders with the tube 12 extending concentrically relative to the tube 14. Other geometrical configurations of and positional relationships between the gas permeable tube 12 and the glass tube 14 may be utilized in accordance with the requirements of particular applications of the invention.

If not formed from a photocatalytic materiel, the gas permeable tube 12 has a light-activated catalyst layer 16 formed on the exterior surface thereof. The catalyst layer 16 is preferably a titanium-based catalyst; however, it will be understood that any light-activated catalyst which forms hydroxyl radicals from water may be utilized in the practice of the invention, if desired. A plurality of electromagnetic radiation sources 18, such as ultraviolet lamps, are positioned around the exterior of the glass tube 14, it being understood that while only one source 18 is illustrated in FIG. 1, in actual practice a plurality of energy sources 18 are employed and are disposed around the entire periphery of the tube 14. As illustrated by the waves 20 in FIG. 1, the sources 18 generate energy in the form of, for example, ultraviolet light which is directed through the glass tube 14 and onto the catalyst layer 16 formed on the exterior surface of the gas permeable tube 12.

In the operation of the apparatus for manufacturing methanol 10, a quantity of water is received in a reservoir 22. Water from the reservoir 22 is directed into the annular space between the gas permeable tube 12 and the glass tube 14 through piping 24. During the operation of the apparatus 10 water flows through the annulus between the gas permeable tube 12 and the glass tube 14 on a continuous basis.

A quantity of methane or natural gas is stored in a reservoir 26. In the operation of the apparatus 10, gas is directed from the reservoir 26 into the interior of the gas permeable tube 12 through piping 28. The gas within the gas permeable tube 12 is maintained at a pressure high enough to cause the gas to pass through the walls of the tube 12 into the water and to prevent the flow of water into the interior of the tube 12.

In the operation of the apparatus for manufacturing methanol 10, the water flowing through the annular space between the gas permeable tube 12 and the glass tube 14 causes gas bubbles to be continuously stripped off the exterior surface of the tube 12. In this manner the size of the gas bubbles is maintained in the sub-micron range. The sub-micron size of the gas bubbles provides an enormous methane surface area which in turn results in unprecedented reaction efficiency.

As the sub-micron size gas bubbles are produced by the flow of water over the exterior surface of the gas permeable tube 12, energy from the sources 18 continuously engages the catalyst layer 16 formed on the exterior of the tube 12. This generates hydroxyl radicals in the flowing water. It is theorized that the hydroxyl radicals homolytically cleave one or more of the carbon-hydrogen bonds in the methane thereby forming either molecules of hydrogen or molecules of water, depending upon the initiating radical, and methyl radicals. The methyl radicals combine either with the hydroxyl radicals to form methanol or with the hydrogen radicals to form methane.

Those skilled in the art will appreciate the fact that other chemical reactions are possible in the operation of the apparatus for manufacturing methanol 10. For example there exists the possibility of a methyl-methyl radical reaction, and also the possibility of a hydrogen-hydrogen radical reaction. Both of these possibilities are extremely remote due to the relatively low concentrations of methyl radicals and hydrogen radicals at any given time.

It will be further understood that natural gas typically comprises up to 10% ethane and up to 2% propane in addition to methane. Therefore, if natural gas is used in the practice of the invention, the reaction products include ethanol, normal propanol, and isopropanol in addition to methanol.

The water flowing from the annulus between the gas permeable tube 12 and the glass tube 14 having the reaction products contained therein is directed to a distillation apparatus 30 through piping 32. The distillation apparatus 30 separates the outflow from the space between the tube 12 and the tube 14 into at least four streams, including a stream of unreacted methane 34 which is returned to the reservoir 26, a stream of water 36 which is returned to the reservoir 22, a stream of other reaction products 38 which are recovered, and a stream of methanol 40. The stream of other reaction products 38 may be further separated into its component parts, if desired.

The present invention further comprises a method of making methanol. In accordance with the method there is provided a continuously flowing stream of water. Sub-micron size bubbles of methane are continuously injected into the flowing water. Hydroxyl radicals are continuously generated from the water. It is theorized that the hydroxyl radicals cleave the hydrogen-carbon bonds of the methane to form methyl radicals. The methyl radicals combine with the hydroxyl radicals to form methanol.

In accordance with more specific aspects of the method, a gas permeable tube having a catalytic layer on the exterior surface thereof is positioned within a glass tube. Water is directed through the annulus between the gas permeable tube and the glass tube, and methane or natural gas is directed into the interior of the gas permeable tube. The water flowing between the gas permeable tube and the glass tube continuously strips sub-micron size bubbles from the exterior surface of the gas permeable tube.

Electromagnetic radiation from, for example, ultraviolet lamps is directed through the glass tube and engages the catalytic surface on the exterior of the gas permeable tube, thereby forming hydroxyl radicals from the flowing water. It is theorized that the hydroxyl radicals homolytically cleave one or more of the carbon-hydrogen bonds in the methane to form either molecules of hydrogen or molecules of water, and methyl radicals. The methyl radicals combine either with the hydroxyl radicals to form methanol or with the hydrogen radicals to form methane. Ethanol and propanol are also produced if natural gas is used in the process.

The use of an internal gas permeable partition cylinder is shown in FIG. 1. One skilled in the art would also recognize that a vast number of shapes and orientations could be used to accomplish the same purpose. For example, the glass tube 14 does not need to be shaped as a tube in order to be functional as a housing. In fact, such a housing need only be partially transparent to electromagnetic radiation for the apparatus to function. Additionally, the orientation of the gas inside an inner tube with water between the inner tube and a housing is not required. One skilled in the art could envision a housing bisected by a gas permeable partition creating a water chamber and a gas chamber. The only requirements of such an embodiment is that the water chamber has a water source and a product outlet, which leads to an isolation apparatus, preferably a distillation apparatus; the gas chamber has a gas source; the gas permeable partition has a catalytic layer that is exposed to electromagnetic energy on the water side of the partition; and the gas permeable partition allows the penetration of gas bubbles that are sheared off by the relative movement of water in the water chamber relative to the gas permeable membrane.

Figure 2:
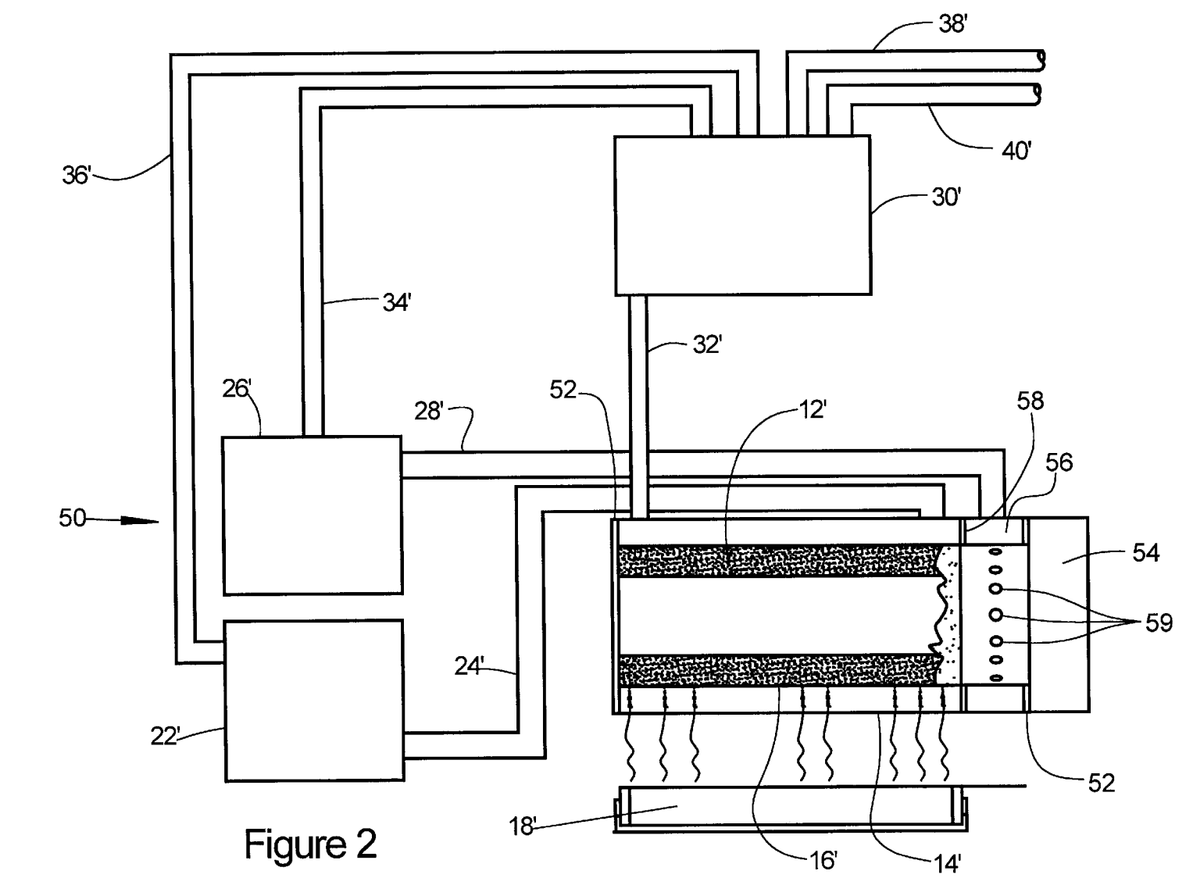
FIG. 2 is a diagrammatic illustration of a second embodiment of the apparatus of the present invention with a rotating sintered stainless steel tube.

Referring now to FIG. 2, there is shown an apparatus for manufacturing methanol comprising a second embodiment of the invention. The apparatus 50 comprises numerous component parts which are substantially identical in construction and function to the apparatus for manufacturing methanol 10 shown in FIG. 1 and described hereinabove in conjunction therewith. Such identical component parts are designated in FIG. 2 with the same reference numerals utilized in the description of the apparatus 10, but are differentiated therefrom by means of a prime (') designation.

In the apparatus for manufacturing methanol 50, the gas permeable tube 12' is supported for rotation relative to the glass tube 14' by sealed bearings 52. Those skilled in the art will appreciate the fact that bearing/seal assemblies comprising separate components may be utilized in the practice of the invention, if desired.

A motor 54 is mounted at one end of the glass tube 14' and is operatively connected to the gas permeable tube 12' to effect rotation thereof relative to the glass tube 14'. The glass tube 14' includes an end portion 56 which is isolated from the remainder thereof by a seal 58. The portion of the tube 12' extending into the end portion 56 of the glass tube 14' is provided with a plurality of uniform or nonuniform apertures 60.

In the operation of the apparatus for manufacturing methanol 50, methane or natural gas is directed from the reservoir 26' through the piping 28', through the end portion 56 of the glass tube 14' and through the apertures 59 into the interior of the gas permeable tube 12'. Water flows from the reservoir 22' through the piping 24' and into the portion of the glass tube 14' that is isolated from the end portion 56 by the seal 58. Water flows out of the glass tube 14' through piping 32' to the distillation apparatus 30'.

The operation of the apparatus for manufacturing methanol 50 of FIG. 2 differs from the operation of the apparatus for manufacturing methanol 10 of FIG. 1 in that in the operation of the apparatus 50, the relative movement between the bubbles forming on the surface of the gas permeable tube 12' and the water contained within the glass tube 14' is controlled by the motor 54 rather than the flow rate of the water as it passes through the glass tube 14'. This is advantageous in that it allows the gas permeable tube 12' to be rotated at a relatively high velocity relative to the water contained within the glass tube 14', thereby assuring that sub-micron size bubbles will be sheared from the surface of the gas permeable tube 12'. Meanwhile, the velocity of the water passing through the interior of the glass tube 14' can be relatively slow, thereby assuring a maximum number of sub-micron size bubbles entering the water per unit volume thereof.

Figure 3:
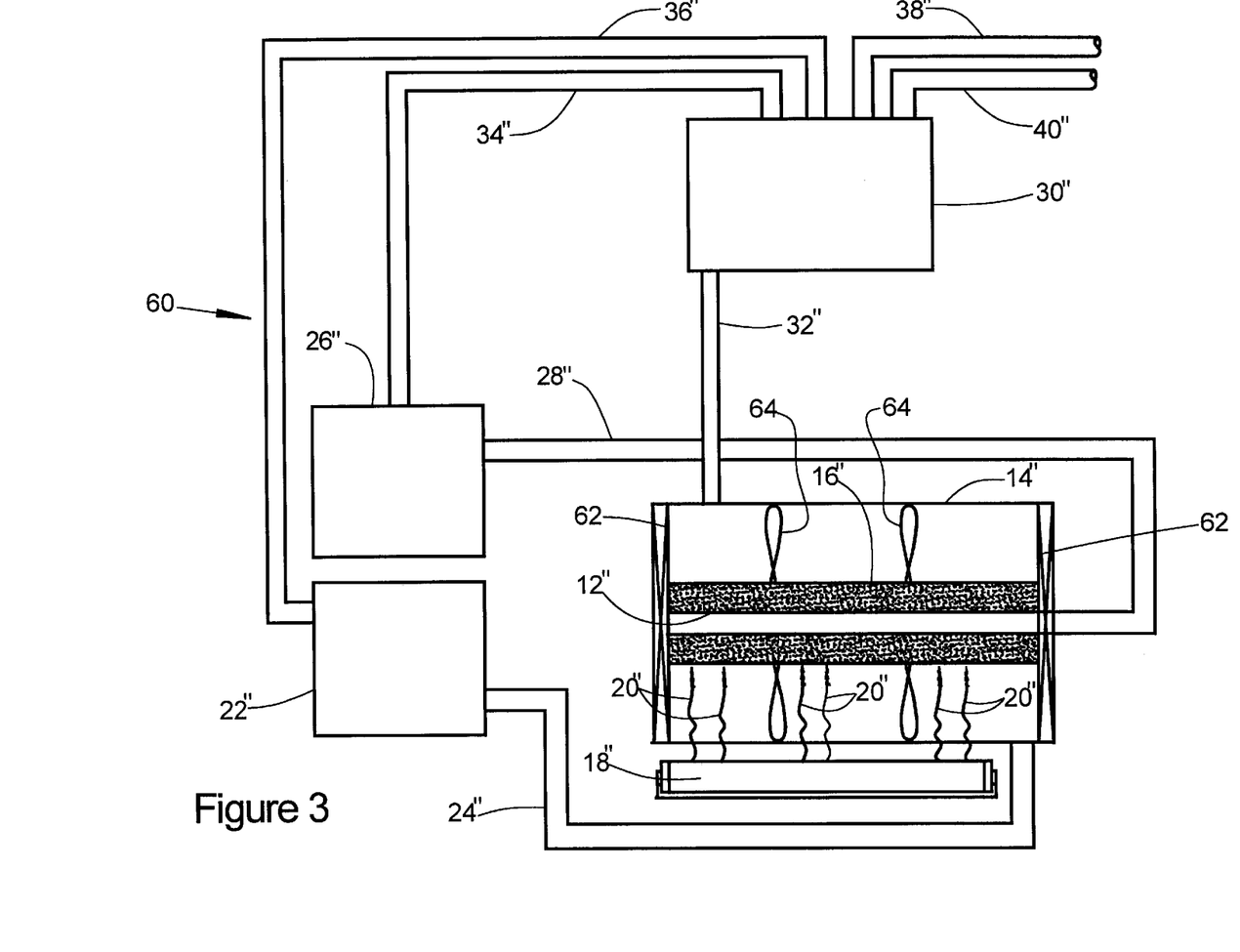
FIG. 3 is a diagrammatic illustration of a third embodiment of the apparatus of the present invention with a rotating sintered stainless steel tube with turbines.

An apparatus for manufacturing methanol comprising a third embodiment of the invention is illustrated in FIG. 3. The apparatus for manufacturing methanol 60 comprises numerous component parts which are substantially identical in construction and function to component parts of the apparatus for manufacturing methanol 10 illustrated in FIG. 1 and described hereinabove in conjunction therewith. Such identical component parts are designated in FIG. 3 with the same reference numerals utilized in the description of the apparatus 10, but are differentiated therefrom by means of a double prime (") designation.

The apparatus for manufacturing methanol 60 comprises a gas permeable tube 12" which is supported for rotation relative to the glass tube 14" by sealed bearings 62. Those skilled in the art will appreciate the fact that the apparatus 60 may be provided with bearing/seal assemblies comprising separate components, if desired.

The gas permeable tube 12" is provided with one or more turbines 64. The pitch of the turbines 64 is adjusted to cause the tube 12" to rotate at a predetermined speed in response to a predetermined flow rate of water through the glass tube 14".

Similarly to the apparatus for manufacturing methanol of FIG. 2, the use of the apparatus for manufacturing methanol 60 is advantageous in that the gas permeable tube 12 " can be caused to rotate relatively rapidly in response to a relatively low flow rate of water through the glass tube 14". This assures that sub-micron size bubbles will be stripped from the outer surface of the gas permeable tube 12" and that a maximum number of bubbles will be received in the water flowing through the glass tube 14" per unit volume thereof. The use of the apparatus for manufacturing methanol 60 is particularly advantageous in applications of the invention wherein water flows through the system under the action of gravity, in that the use of the turbines 64 eliminates the need for a separate power source to effect rotation of the gas permeable tube 12" relative to the glass tube 14".

Figure 4:
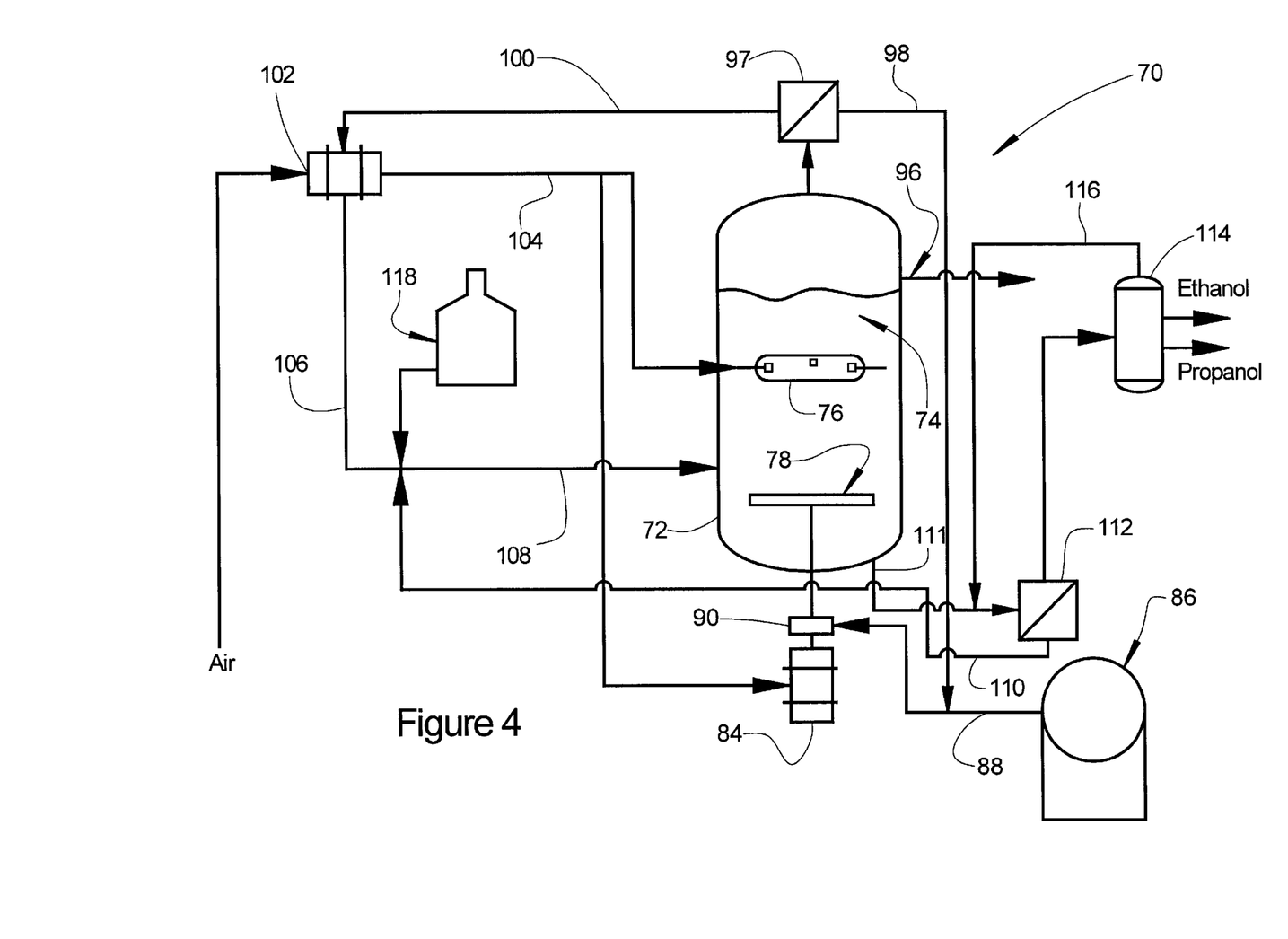
FIG. 4 is a diagrammatic illustration of a fourth embodiment of the apparatus of the present invention.
Figure 5:
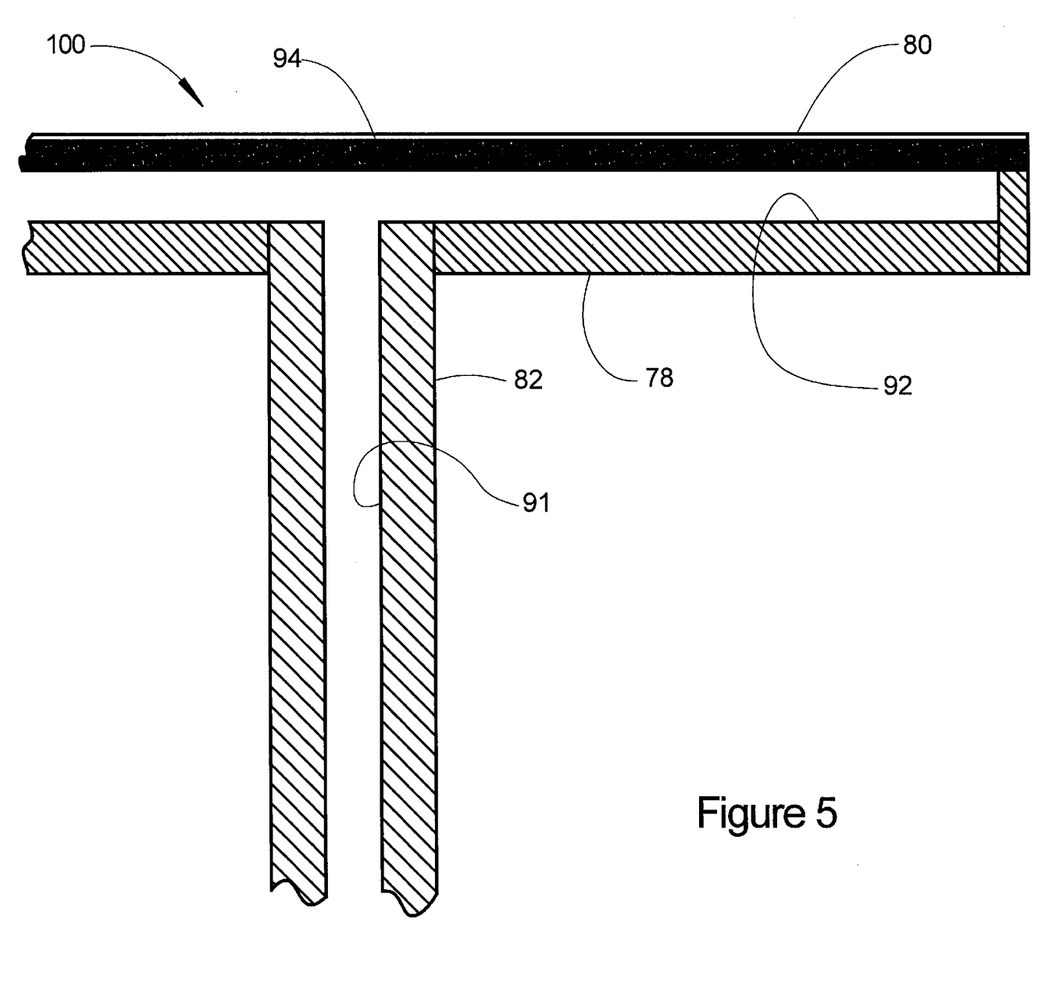
FIG. 5 is an enlargement of a portion of FIG. 4.

Referring now to FIGS. 4 and 5, there is shown a method of and apparatus for manufacturing methanol and other alcohols 70 comprising a fourth embodiment of the invention. In accordance with the fourth embodiment of the invention, there is provided a distillation unit 72 comprising a tank having a quantity of water 74 contained therein. One or more electromagnetic radiation sources 76 are also positioned in the tank 72. The distillation unit 72 includes a heat source, which may comprise the radiation sources 76, sufficient to effect distillation of methanol and other alcohols from water.

A hollow disk 78 is mounted in the lower portion of the tank 72. As is best shown in FIG. 5, the disk 78 includes a gas permeable partition 80 supported on a tube 82 for rotation within the tank 72 under the operation of a motor 84. The partition 80 may comprise sintered stainless steel, sintered glass, or sintered ceramic materials, or may be formed entirely from a catalytic material, depending upon the requirements of particular applications of the invention. Natural gas received from a supply 86 is directed through piping 88 and a suitable commutator 90 into the tube 82 and through the tube 82 into the interior of the hollow disk 78. The tube 82 has a hollow interior 91 and the disk 78 has a hollow interior 92 connected in fluid communication therewith. The gas permeable partition 80 is coated with a light-activated catalytic layer 94.

The disk 78 is supplied with natural gas at a pressure just high enough to overcome the head pressure of the water 74. The disk 78 is rotated by the motor 84 at an appropriate speed in contact with the water 74 such that a shearing phenomenon occurs at the surface of the catalytic layer 94 thus producing bubbles of natural gas of extremely small size. The extreme small size of the bubbles thus produced results in a surface area to volume ratio of small bubbles which significantly improves the efficiency of the reaction.

As the sub-micron size gas bubbles are produced by movement of the exterior surface of the gas permeable partition 80 in the water 74, electromagnetic energy from the sources 76 continuously engages the catalytic surface 94 formed on the exterior of the partition 80, it being understood that depending on the characteristics of the catalytic layer 94, energy comprising various portions of the electromagnetic spectrum may be used in the practice of the invention.

Activation of the catalytic layer 94 generates hydroxyl radicals in the water. It is theorized that the hydroxyl radicals homolytically cleave one or more of the carbon-hydrogen bonds in the methane, ethane, propane, etc., thereby forming either molecules of hydrogen or molecules of water, depending upon the initiating radical, and methyl, ethyl, and propyl radicals which combine either with the hydroxyl radicals to form methanol, ethanol, and propanol, or with the hydrogen radicals to form methane, ethane, and propane.

The methanol produced by the operation of the distillation unit 72 is recovered at outlet 96. A pressure swing absorber 97 receives natural gas and hydrogen from the distillation unit 72. Unreacted natural gas is recovered from the pressure swing absorber 97 at outlet 98 and is returned to the distillation unit 72 through piping 88. By-product hydrogen produced in the distillation unit 72 is recovered at outlet 100 and is directed to a fuel cell 102.

Within the fuel cell 102, hydrogen recovered from the distillation unit 72 is combined with oxygen from the atmosphere to produce electricity which is recovered at terminal 104 and water which is recovered at outlet 106 and returned to the distillation unit 72 through piping 108. As will be appreciated by those skilled in the art, a conventional engine/generator may be used in lieu of the fuel cell 102; however, the use of a fuel cell is preferred due to its greater efficiency.

The use of the hydrogen recovered from the distillation unit 72 to produce electricity comprises an important advantage in the use of the present invention in that the electricity thus produced may be utilized to provide artificial lighting in those instances in which the apparatus 70 is situated at a remote location and/or to provide heating for the distillation unit 72. As is shown in FIG. 4, electricity from the fuel cell 102 may also be used to operate the radiation sources 76 and the motor 84.

In addition to producing methanol, the apparatus 70 converts other alkanes present in the natural gas to their respective alcohols, namely: ethanol, normal propanol, and isopropanol. The higher alcohols thus produced are recovered from the distillation unit 72 at outlet 111 and are directed to a reverse osmosis unit 112, and from the reverse osmosis unit 112 to a secondary distillation unit 114 to produce purer forms of the higher alcohols. Like the distillation unit 72, the distillation unit 114 is provided with a heat source adequate to effect the desired distillation. Unrecovered materials from the secondary distillation unit 114 are returned to the reverse osmosis unit 112 through piping 116. The reverse osmosis unit 112 also produces water which is returned to the distillation unit 72 through the piping 108.

Typically, the water which is returned to the distillation unit 72 from the fuel cell 102 and the reverse osmosis unit 112 is sufficient to maintain a predetermined quantity of water therein. The distillation unit 72 is initially filled from a water supply 118 which is also available to supplement the water received from the fuel cell 102 and the reverse osmosis unit 112 if necessary to maintain an adequate supply of water in the distillation unit 72.

In lieu of the motor 84, the disk 78 may be oscillated using a torsion motor or reciprocated using a motor and crank assembly. Other apparatus for effecting relative movement between the partition 80 and the water 74 will suggest themselves to those skilled in the art.

Figure 6:
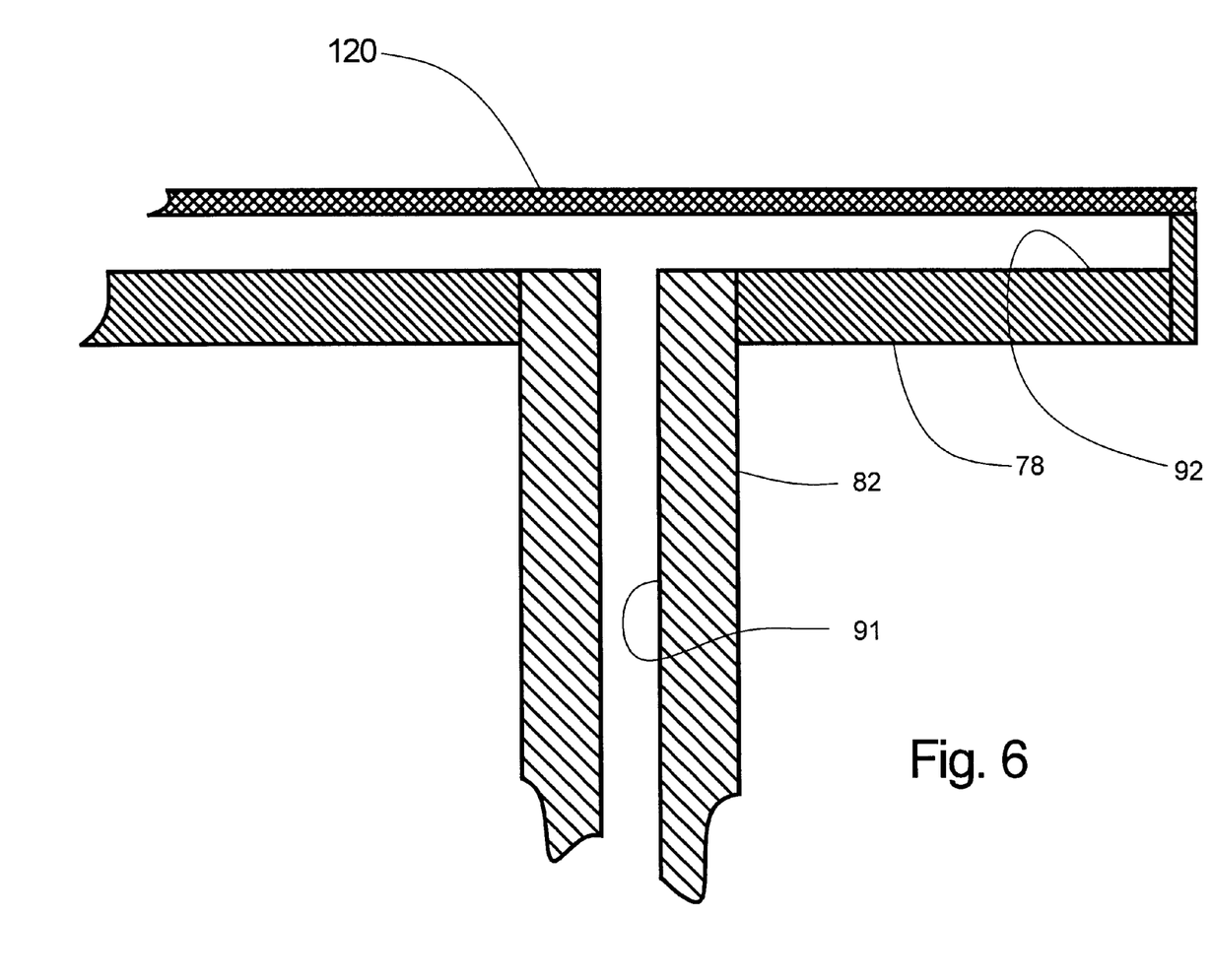
FIG. 6 is an illustration similar to FIG. 5 showing an alternative construction useful in the practice of the invention.

As will be appreciated by those skilled in the art, it is known to produce gas permeable partitions entirely from photocatalytic material, including titanium-based catalytic materials. FIG. 6 illustrates a hollow disk 78 having a gas permeable partition 120 formed entirely from one or more catalytic materials. Such construction eliminates the need of forming a catalytic layer on the surface of a gas permeable partition.

Those skilled in the art will appreciate the fact that the method and apparatus of the present invention can be utilized to convert gases other than methane and natural gas into valuable products. For example, the method and apparatus of the present invention can be utilized to convert carbon dioxide to methanol and methane. The adaptation of other chemical processes to the method and apparatus of the present invention will readily suggest themselves to those skilled in the art.

Although preferred embodiments of the invention have been illustrated in the accompanying Drawings and described in the foregoing Detailed Description, it will be understood that the invention is not limited to the embodiments disclosed but is capable of numerous rearrangements, modifications, and substitutions of parts and elements without departing from the spirit of the invention.

I claim:

1. An apparatus for manufacturing methanol and higher alcohols from natural gas and water comprising:

a hollow chamber positioned in the water and including a gas permeable partition engaging the water;

a solid gas permeable electromagnetic radiation-activated catalytic layer comprising at least the exterior of the gas permeable partition;

means for continuously causing relative movement between the exterior surface of the solid gas permeable catalytic layer and the water;

means for maintaining natural gas within the interior of the hollow chamber at a predetermined pressure sufficient to cause gas flow through the gas permeable partition/solid gas permeable catalytic layer for entrainment in the water as sub-micron size bubbles while preventing water flow therethrough;

means for directing electromagnetic radiation energy onto the catalytic layer thereby forming hydroxyl radicals from the water;

methyl, ethyl, and propyl radicals from the natural gas combining with the hydroxyl radicals to form methanol, ethanol, and propanol.

2. The apparatus for manufacturing methanol and higher alcohols from natural gas according to claim 1 wherein the gas permeable partition comprises a sintered stainless steel partition.

3. The apparatus for manufacturing methanol and higher alcohols from natural gas according to claim 1 wherein the gas permeable partition comprises a sintered glass partition.

4. The apparatus for manufacturing methanol and higher alcohols according to claim 1 wherein the gas permeable partition comprises a sintered ceramic partition.

5. The apparatus for manufacturing methanol and higher alcohols from natural gas according to claim 1 wherein the gas permeable partition comprises a partition formed entirely from catalytic material.

6. The apparatus for manufacturing methanol and higher alcohols from natural gas according to claim 1 wherein the catalytic material is a photocatalytic material which is responsive to electromagnetic radiation within the portion of the electromagnetic spectrum comprising visible light and ultraviolet radiation.

7. The apparatus for manufacturing methanol and higher alcohols from natural gas according to claim 1 wherein the means for causing relative movement between the gas permeable partition and the water comprises means for rotating the gas permeable partition relative to the water.

8. The apparatus for manufacturing methanol and higher alcohols from natural gas according to claim 1 wherein the means for causing relative movement between the gas permeable partition and the water comprises means for oscillating the gas permeable partition relative to the water.

9. The apparatus for manufacturing methanol and higher alcohols from natural gas according to claim 1 wherein the means causing relative movement between the gas permeable partition and the water comprises apparatus for reciprocating the gas permeable partition relative to the water.

10. The apparatus for manufacturing methanol and higher alcohols from natural gas according to claim 1 wherein the for causing relative movement between the gas permeable partition and the water comprises means for causing the water to flow over the exterior of the gas permeable partition.

11. The apparatus according to claim 1 wherein the activation of the catalyst also produces hydrogen and further including means for directing the hydrogen to a fuel cell which uses the hydrogen as fuel to produce electricity.

12. An apparatus for manufacturing methanol from methane and water comprising:
    a hollow chamber including a gas permeable partition positioned in the water;
    a solid gas permeable catalytic layer comprising at least the exterior of the gas permeable partition;
    means for continuously causing relative movement between the exterior surface of the solid gas permeable photocatalytic layer and the water;
    means for maintaining methane within the interior of the hollow chamber at a predetermined pressure sufficient to cause methane to flow through the gas permeable partition/solid gas permeable catalytic layer for entrainment as sub-micron size bubbles in the water while preventing water flow therethrough;
    means for directing energy onto the catalytic layer thereby forming hydroxyl radicals from the water;
    methyl radicals from the methane combining with the hydroxyl radicals to form methanol.

13. The apparatus for manufacturing methanol from methane according to claim 12 wherein the gas permeable partition comprises a sintered stainless steel partition.

14. The apparatus for manufacturing methanol from methane according to claim 12 wherein the gas permeable partition comprises a sintered glass partition.

15. The apparatus for manufacturing methanol according to claim 12 wherein the gas permeable partition comprises a sintered ceramic partition.

16. The apparatus for manufacturing methanol from methane according to claim 12 wherein the gas permeable partition comprises a partition formed entirely from catalytic material.

17. The apparatus for manufacturing methanol from methane according to claim 12 wherein the catalytic material is a photocatalytic material which is responsive to electromagnetic radiation within the portion of the electromagnetic spectrum comprising visible light and ultraviolet radiation.

18. The apparatus for manufacturing methanol from methane according to claim 12 wherein the means for causing relative movement between the gas permeable partition and the water comprises means for rotating the gas permeable partition relative to the water.

19. The apparatus for manufacturing methanol from methane according to claim 12 wherein the means for causing relative movement between the gas permeable partition and the water comprises means for oscillating the gas permeable partition relative to the water.

20. The apparatus for manufacturing methanol from methane according to claim 12 wherein the means causing relative movement between the gas permeable partition and the water comprises means for reciprocating the gas permeable partition relative to the water.

21. The apparatus for manufacturing methanol from methane according to claim 12 wherein the means for causing relative movement between the gas permeable partition and the water comprises means for causing the water to flow over the exterior of the gas permeable partition.

22. The apparatus according to claim 12 wherein the activation of the catalyst also produces hydrogen and further including means for directing the hydrogen to a fuel cell which uses the hydrogen as fuel to produce electricity.

23. An apparatus for manufacturing methane and higher alcohols from natural gas and water comprising:
    a hollow chamber having a sintered partition positioned in the water;
    a solid gas permeable catalytic layer formed on the exterior of the sintered partition;
    means for continuously causing relative movement between the exterior surface of the solid gas permeable photocatalytic layer and the water;
    means for maintaining natural gas within the interior of the chamber at a predetermined pressure sufficient to cause natural gas to flow through the sintered partition and the solid gas permeable catalytic layer for entrainment as sub-micron size bubbles in the water while preventing water flow therethrough;
    means for directing energy onto the solid gas permeable catalytic layer on the exterior of the sintered partition thereby forming hydroxyl radicals in the water;
    methyl, ethyl, and propyl radicals from the natural gas combining with the hydroxyl radicals to form methanol, ethanol and propanol.

24. The apparatus for manufacturing methanol and higher alcohols from natural gas according to claim 23 wherein the sintered partition comprises sintered stainless steel.

25. The apparatus for manufacturing methanol and higher alcohols from natural gas according to claim 23 wherein the sintered partition comprises sintered glass.

26. The apparatus for manufacturing methanol and higher alcohols from natural gas according to claim 23 wherein the ceramic partition comprises ceramic stainless steel.

27. The apparatus for manufacturing methanol and higher alcohols from natural gas according to claim 23 wherein the layer of catalytic material comprises a layer of photocatalytic material which is responsive to ultraviolet radiation.

28. The apparatus for manufacturing methanol and higher alcohols from natural gas according to claim 23 wherein the layer of catalytic material is responsive to visible light.

29. The apparatus for manufacturing methanol and higher alcohols from natural gas according to claim 23 wherein the means for causing relative movement between the sintered partition and the water causes rotation between the sintered partition and the water.

30. The apparatus for manufacturing methanol and higher alcohols from natural gas according to claim 23 wherein the means for causing relative movement between the sintered partition and the water causes oscillation between the sintered partition and the water.

31. The apparatus for manufacturing methanol and higher alcohols from natural gas according to claim 23 wherein the means for causing relative movement between the sintered partition and the water causes reciprocation between the sintered partition and the water.

32. The apparatus for manufacturing methanol and higher alcohols from natural gas according to claim 23 wherein the relative movement between the partition and the water results from water flow over the exterior of the partition.

33. The apparatus according to claim 23 wherein the activation of the catalyst also produces hydrogen and further including apparatus for directing the hydrogen to a fuel cell which uses the hydrogen as fuel to produce electricity.

34. An apparatus for manufacturing methanol and methane from carbon dioxide comprising:

a quantity of water;

a hollow chamber positioned in the water and including a gas permeable partition engaging in the water;

a solid gas permeable catalytic layer comprising at least the exterior of the gas permeable partition;

means for continuously causing relative movement between the exterior surface of the solid gas permeable photocatalytic layer and the water;

means for maintaining carbon dioxide within the interior of the hollow chamber at a predetermined pressure sufficient to cause carbon dioxide to flow through the gas permeable partition and the solid gas permeable catalytic layer for entrainment as sub-micron size bubbles in the water while preventing water flow therethrough;

means for directing energy onto the catalytic layer thereby forming hydroxyl and hydrogen radicals from the water;

the hydroxyl and hydrogen radicals from the water combining with carbon radicals from the carbon dioxide to form methanol and methane.

* * * * *